US008288726B2

(12) United States Patent  
Weil

(10) Patent No.: US 8,288,726 B2  
(45) Date of Patent: Oct. 16, 2012

(54) REMOTE SENSING OF SUBSURFACE ARTIFACTS BY USE OF VISUAL AND THERMAL IMAGERY

(76) Inventor: Gary J. Weil, St. Louis, MO (US)

( * ) Notice: Subject to any disclaimer, the term of this patent is extended or adjusted under 35 U.S.C. 154(b) by 453 days.

(21) Appl. No.: 12/448,318

(22) PCT Filed: Dec. 18, 2007

(86) PCT No.: PCT/US2007/025781
§ 371 (c)(1),
(2), (4) Date: Jun. 17, 2009

(87) PCT Pub. No.: WO2008/100308
PCT Pub. Date: Aug. 21, 2008

(65) Prior Publication Data
US 2010/0025582 A1 Feb. 4, 2010

Related U.S. Application Data

(60) Provisional application No. 60/875,787, filed on Dec. 19, 2006.

(51) Int. Cl.
*G01J 5/02* (2006.01)
(52) U.S. Cl. .................. 250/339.01; 250/338.1

(58) Field of Classification Search ............... 250/338.1, 250/339.01
See application file for complete search history.

(56) References Cited

U.S. PATENT DOCUMENTS

| 4,910,593 | A | * | 3/1990 | Weil | 348/164 |
| 5,836,398 | A | * | 11/1998 | White | 169/24 |
| 7,363,157 | B1 | * | 4/2008 | Hanna et al. | 702/5 |
| 2002/0018510 | A1 | * | 2/2002 | Murphy et al. | 374/45 |
| 2003/0047683 | A1 | * | 3/2003 | Kaushal | 250/330 |
| 2006/0018642 | A1 | * | 1/2006 | Chaplin | 396/7 |

* cited by examiner

*Primary Examiner* — David Porta
*Assistant Examiner* — Casey Bryant
(74) *Attorney, Agent, or Firm* — Peter S. Gilster; Greensfelder, Hemker & Gale, P.C.

(57) ABSTRACT

Methodology, systems, and apparatus for remote sensing as by detection and mapping of subsurface artifacts including clandestine tunnels and other subterranean facilities that may carry enemy soldiers, terrorists, weapons, munitions and explosives and other material of war or terrorism by use of visual and thermal imagery, specifically including the use of infrared (IR) thermography and related analysis, including visual imagery and its analysis including correlation between IR thermography data, visual data and other information which can be taken into consideration in relation to IR thermography data and visual data. Various types of data enhancements may be used to assist in target detection.

7 Claims, 2 Drawing Sheets

REMOTE SENSING OF SUBSURFACE ARTIFACTS BY USE OF VISUAL AND THERMAL IMAGERY

CROSS-REFERENCE TO RELATED APPLICATION(S)

This application claims the priority of U.S. Provisional Patent Provisional 60/875,787 filed Dec. 19, 2006, of the present inventor, Gary J. Weil, P.E., C.P.I.M., entitled REMOTE SENSING OF SUBSURFACE ARTIFACTS BY USE OF VISUAL AND THERMAL IMAGERY, the entirety of which is herein incorporated by reference.

BACKGROUND AND SUMMARY

1. Field of the Invention

The invention relates to sensing of subsurface artifacts by use of visual and thermal imagery and more particularly to remote sensing of such subsurface artifacts as may be exemplified by tunnels and excavations.

2. Related Art

Methods and systems for detection of subterranean anomalies such as voids and leaks by the use of infrared thermography and, more particularly, to methods and system for using infrared thermography together with ground penetrating radar to map subterranean leakage voids and to repair such voids and terminate such leakage are the subject of U.S. Pat. No. 7,218,267 issued May 15, 2007, on application Ser. No. 11/442,508, filed May 26, 2006, and which patent is entitled SYSTEM OF SUBTERRANEAN ANOMALY DETECTION AND REPAIR USING INFRARED THERMOGRAPHY AND GROUND PENETRATING RADAR, based Upon U.S. Provisional App. No. 60/685,338, filed May 27, 2005; and corresponding PCT Patent Application entitled SYSTEM OF SUBTERRANEAN ANOMALY DETECTION AND REPAIR, filed May 26, 2006, both of the present inventor, and both of which are herein incorporated in their entirety by reference, and such patent applications broadly relate to methods and systems for detection of subterranean anomalies such as voids and leaks by the use of infrared thermography and, more particularly, to methodology, systems, and apparatus for using infrared thermography together with ground penetrating radar to map subterranean leakage voids and to repair such voids and terminate such leakage in a very highly accurate, reliable, rapid and cost-effective manner.

The present inventor is also the patentee of Weil U.S. Pat. No. 4,910,593 issued Mar. 20, 1990, entitled SYSTEM FOR GEOLOGICAL DEFECT DETECTION UTILIZING COMPOSITE VIDEO-INFRARED THERMOGRAPHY, and various corresponding patents in other countries. U.S. Pat. No. 4,910,593, the entirety of which is herein incorporated in its entirety by reference, discloses a selectively mobile system with an infrared ("IR") scanner and video camera having a common area of focus and apparatus for detecting location permits detection of subterranean geological anomalies. Infrared and visual images are simultaneously successively recorded on videotape together with related location data and other relevant information. Video recorded infrared, video and location data are selectively captured on successive frames. Such frames are recorded for further analysis such as for determining the location and extent of subsurface anomalies such as leaks. That system is especially useful for mapping such anomalies along a route of travel, as across bridges, highways and other traffic surfaces such as paved surfaces or for examining surfaces that extend over elongated passages such as buried sewer and water lines, and for finding bridge and pavement faults and defects.

These various prior systems and variations and developments of the present inventor, as implemented commercially on a national and international basis by the present inventor at EnTech Engineering, Inc., are known as the INSITE I, II, III, IV, V & VI Subsurface Pipeline Leak and Erosion Void Detection Systems or more simply as the INSITE I, II, III, IV, V & VI Systems.

BACKGROUND RELATIVE TO THE INVENTION

Over the past 200 years whole new worlds have been established below ground in the form of tunnels, storage tanks, rooms and buildings built for safety and clandestine purposes as well as various civilization required utilities such as electric, water, chemical and fuel. In civilian markets, utility tunnels carrying power, communications, water, sewer and chemical pipelines have been built between buildings, coal chutes have been built to allow coal to be delivered to building basement boilers, and electrical rooms have been built to supply power to facilities of all kinds. Construction of all types requires knowledge of these subsurface artifacts for both safety and economic reasons.

Military and domestic security departments around the world, such as the U.S. Homeland Security Department, have established high priority needs for locating tunnels capable of being used to allow illegal immigrants to cross under national borders or to move and/or store illegal drugs and/or weapons, as well as underground facilities such as storage areas, access points and production facilities for the storage of munitions and other ordnance and other objects and matter of military significance, including space exploration, as on planets. In almost all instances, no "as-built" engineering drawings or mapping information exists because of age, lack of funding, or purpose.

As the technological and political world changes vast civilian and military and space needs have been established to locate these hidden tunnels, storage areas, access points and production facilities. As civilian buildings are upgraded or new facilities built, many problems, and their often-enormous costs, could be minimized if these hidden subsurface facilities and utilities could be detected and accurately mapped prior to the design or construction phases of a project. If hidden national border crossing tunnels could be located and mapped, they could be eliminated. This could save enormous money and manpower costs in crime control, welfare costs, and political needs and human lives. In military campaigns, both in the USA and around the world, the detection and mapping of clandestine tunnels and other subterranean facilities that may carry enemy soldiers, terrorists, weapons, munitions and explosives and other materiel of war or terrorism could save many lives and mean the difference between success and failure in our country's efforts in such places in other countries where there is open conflict.

SUMMARY

Among the objects, features, advantages and benefits of the present invention are the provision of advantageous methodology, systems, and apparatus for remote sensing of subsurface artifacts by use of visual and thermal imagery, specifically including the use of infrared (IR) thermography and related analysis, including visual imagery and its analysis including correlation between IR thermography data, visual data and other information which can be taken into consideration in relation IR thermography data and visual data.

Among specific benefits of the new methodology, systems, and apparatus are that investigation techniques are non-invasive and non-destructive. Personnel involved in implementing the methodology, systems, and apparatus do not need to dig up streets, attach cables to underground utilities, insert pigs into pipelines or inconvenience the public. Customized equipment and data collection vans or aerial means can be used to implement the new methodology, systems, and apparatus wherein the vans as herefore proposed in the '593 patent typically can travel at 5-20 mph (8-32 kph).

Further, the methodology, systems, and apparatus involves IR and visual and related investigations that may take place during either daylight hours or nighttime to reduce traffic that may otherwise cause slowdowns for the data collection van which so as to help increase productivity.

Extremely high productivity is possible in implementation of the new methodology, systems, and apparatus, typically in the range of 15,000-25,000 linear feet (4.572-7.620 km) of contiguous distance per day when using an customized data collection van of the present inventor, depending upon the number of anomalous areas detected and encountered traffic. For cross-country flights, 100-250 miles (161-402.3 km) per day of oil, gas, chemical, and water pipelines or border patrol areas already can be inspected using configured helicopter or unmanned aerial vehicle mounted systems.

Unique data manual and computer enhanced analysis procedures in using the new methodology, systems, and apparatus allow retrieval of image data previously considered unusable because of low contrast, overexposure and under exposure of both visual and thermographic data. Customized computer enhanced analysis procedures may be used on both individual images and video streaming images.

Briefly, methodology, systems, and apparatus herein disclosed is useful for remote sensing as by detection and mapping of subsurface artifacts including clandestine tunnels and other subterranean facilities that may carry enemy soldiers, terrorists, weapons, munitions and explosives and other materiel of war or terrorism by use of visual and thermal imagery, specifically including the use of infrared (IR) thermography and related analysis, including visual imagery and its analysis including correlation between IR thermography data, visual data and other information which can be taken into consideration in relation to IR thermography data and visual data. Various types of data enhancements may be used to assist in target detection.

System, apparatus and method features are disclosed. As exemplary of the thrust of the invention, the system comprises provision in the form of sensors for collecting of infrared (IR) and visual data for imaging to within an area which may have subsurface targets, the sensors producing multi-spectral, bore-sighted images to locate and map specific types of targets such as, but not limited to, tunnels, storage areas, underground chemical tanks, utility pipelines and conduits, construction debris, and roadway and bridge deck asphalt and concrete pavement internal cracks and voids. IR and visual sensors are disclosed, for example in above-referenced Weil U.S. Pat. No. 4,910,593 where they are described as an infrared ("IR") scanner 12 and a video camera 14 carried by a support boom 20 which is attached to a vehicle 22. The IR data is in accordance with the present disclosure collected with temperature pattern thermal resolution of less than 75 milliKelvins (mK) and matching visual imagery; the one or more detectors operating in the range of 400 nm. to 14 µm. The present system further comprises provision for processing and storing the images with both analogue and digital hardware and software. IR and visual data processing and storage are disclosed in above-referenced Weil U.S. Pat. No. 4,910,593 which describes use of a quad processor 32 that transmits the video image data simultaneously to at least one video tape recorder 34. The present system further comprises provision for storage of IR data and analysis and correlation between IR thermography data, visual data and location data and other relevant information which can be taken into consideration in relation to IR thermography data and visual data. Said '593 patent describes operation such that simultaneous with the video 14 recording, the IR scanner 12 detects geological surface temperature levels and variations in the common field of view. The IR image data thus detected are transmitted to a real-time IR data processor 40, of the microprocessor type, where successive images of the IR scans are viewable on an incorporated display screen 40a. As that '593 patent describes, simultaneously, analog form IR image data are converted by a colorizer/analog-to-digital converter 42 to digital form and provided to the quad processor 32 for subsequent selective transmittal to videotape recorder 34, as suitably controlled by a conventional tuner-timer 44. The videotape recorder 34 is used. The IR image data may be simultaneously transferred to another segment 36a of the display screen 36 of the color composite monitor 35 or alternatively viewed on an independent IR monitor 12b. In the Weil '795 patent, elements 10, 12, 14, 16, 18, 20, 22 and 24 will generally be relevant.

Location by LORAN or satellite location generally is described in said '593 patent of detected structural voids or defects, as in pavement.

The present system provides target identification by target signatures depending upon such targets being sought, i.e., which are characteristic of selected targets (such as tunnels of possible military or space exploration significance. The sensing of such subsurface artifacts is further characterized by location and mapping of such subsurface artifacts.

DESCRIPTION OF INVENTIVE EMBODIMENTS

Figure 1:
FIG. 1 is an unprocessed low contrast image of potential subsurface tunnel sites and/or buried sewer pipeline capable of transporting humans.
Figure 2:
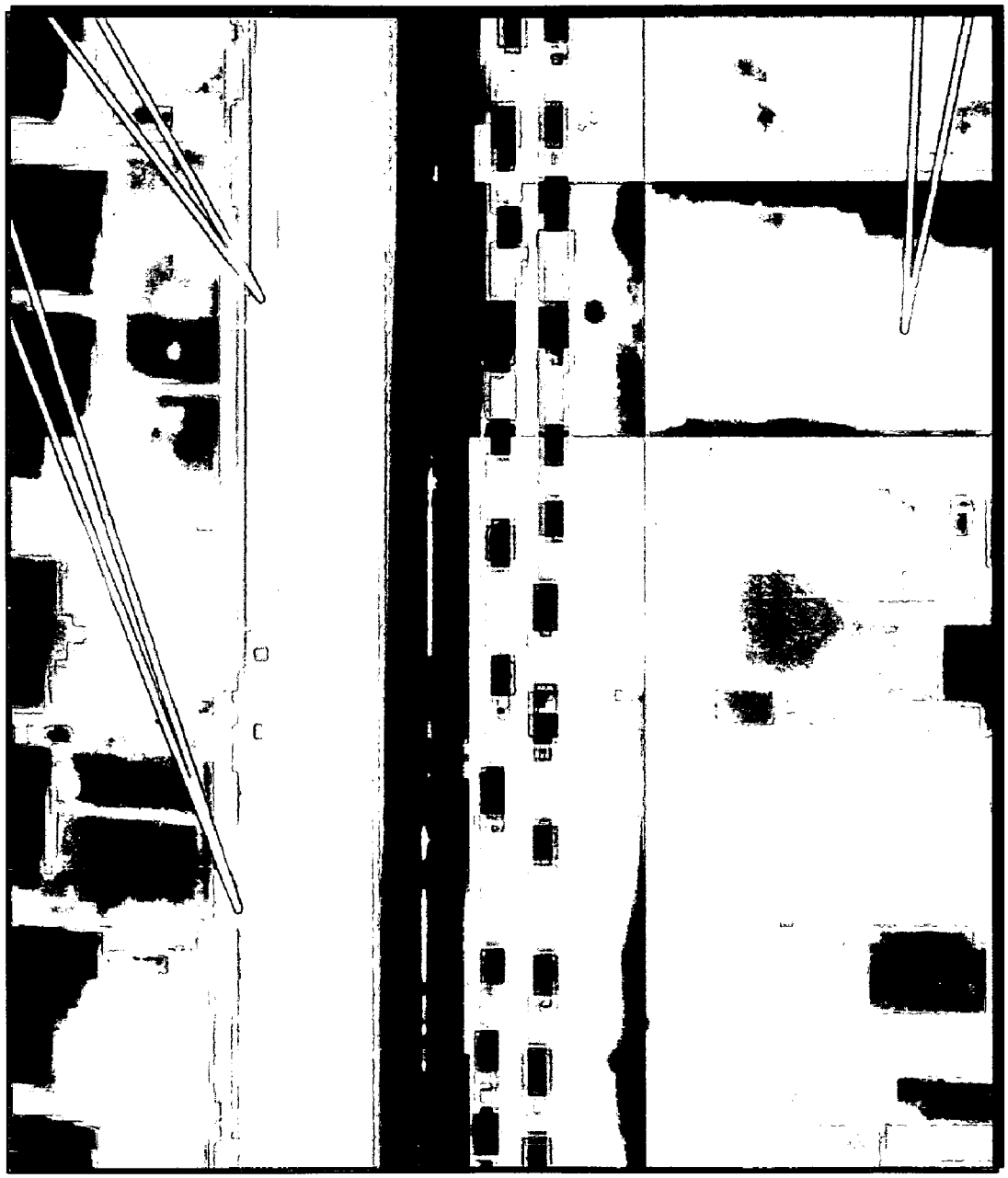
FIG. 2 is an enhanced contrast of such potential subsurface tunnel sites and/or buried sewer pipeline capable of transporting humans.

Specifically, the new remote sensing, non-invasive system, and its apparatus and methodology, is specifically designed to locate subsurface targets including, but not limited to, tunnels, underground storage tanks (USTs), clandestine storage areas and other underground/subterranean facilities where there may be munitions or material of war or crime, including drugs, weapons, munitions, and such facilities may include large pipes such as sewer, water, chemical, oil and gas, capable of allowing human traffic.

The inventive system can be configured to be hand carried, mounted on a van or truck, or mounted beneath an aerial platform either manned rotary wing, fixed wing or Unmanned Aerial Vehicle UAV) of any of various types. The various hardware mounting platforms provide users with capability to investigate small, medium and large size areas, both inside buildings and outside buildings, during both daylight and nighttime hours.

The hardware apparatus of the new system comprises one or more detectors in the 400 nm. to 14 µm. range to produce visual and thermal imagery of ground surfaces. These sensors produce multi-spectral, bore-sighted images to locate and map specific types of targets such as, but not limited to, tunnels, storage areas, underground chemical tanks, utility pipelines and conduits, construction debris, and roadway and bridge deck asphalt and concrete pavement internal cracks and voids. These images differ from traditional IR and visual imagery by using dynamic ranges of only a few degrees rather than the tens or hundreds of degrees normally imaged for traditional IR applications of looking for "hotspots" in electrical panels, boiler leaks, and military snipers in the dark.

Collected imagery provided by the new system and methodology also differs from the existing norm by being required to be collected in accordance with specific procedures and protocol of the present inventor based upon special calibration procedures, special times for data collection, and special thermal range settings based upon proprietary dynamic range settings.

These images are processed and stored with both analogue and digital hardware and software. The systems are designed to collect data with temperature pattern thermal resolution of less than 75 milliKelvins (mK) and matching visual imagery. The images may be in the format of still images, a series of still images, or a video sequence of images. In conjunction with the imaging sensors, various types of global positioning systems (GPS), telemetry transmission systems, and LIDAR systems are attached and used to facilitate target mapping.

Both human and software analysis of the data imagery is used in the new system and methodology to locate special proprietary target signatures depending upon the targets being sought. These thermal patterns reflect areas saturated with fluids and/or air gaps, which affect the surface temperatures because they change the subsurface thermal conductivity and thermal capacity. Various types of data enhancements may be used to assist in target detection, including but not limited to: global and localized contrast, global and localized brightness, image size changes, global and localized blob analysis, pixel by pixel contrast enhancements, colorization, background image noise suppression, and orthorectification, etc.

Is seen accordingly that there is disclosed a system for seeking, by remote sensing, subterranean targets including clandestine tunnels and other subterranean facilities that may carry enemy soldiers, terrorists, weapons, munitions and explosives and other materiel of war or terrorism by use of visual and thermal imagery, comprising provision in the form of sensors for collecting of infrared (IR) and visual data for imaging to within an area which may have subsurface targets, the sensors producing multi-spectral, bore-sighted images to locate and map specific types of targets such as, but not limited to, tunnels, storage areas, underground chemical tanks, utility pipelines and conduits, construction debris, and roadway and bridge deck asphalt and concrete pavement internal cracks and voids. The system further comprises provision for processing and storing the images with both analogue and digital hardware and software. The system further comprises provision for analysis and correlation between IR thermography data, visual data and location data and other relevant information which can be taken into consideration in relation to IR thermography data and visual data. The system thereby provides target identification by target signatures depending upon such targets being sought. The sensing of such subsurface artifacts is further characterized by location and mapping of such subsurface artifacts. The IR data is collected with temperature pattern thermal resolution of less than 75 milliKelvins (mK) and matching visual imagery. The one or more detectors operate in the range of 400 nm. to 14 μm. The images may be in the format of still images, a series of still images, or a video sequence of images.

As apparatus, the invention provides remote sensing of subsurface target artifacts by use of visual and thermal imagery, comprising (a) provision for infrared (IR) thermography and for related analysis, including visual imagery; (b) provision for correlation between IR thermography data and visual data which can be taken into consideration in relation IR thermography data and visual data; and (c) provision for correlation of the IR data and visual data with location data and other relevant information other information; whereby to sense and identify target artifacts which are of military or space exploration significance.

The artifacts to be sensed are targets such as, but not limited to, clandestine tunnels and other subterranean facilities that may carry enemy soldiers, terrorists, weapons, munitions and explosives and other materiel of war or terrorism.

From the foregoing description, it is seen that the invention provides a novel method of identifying and mapping, as subsurface targets, clandestine tunnels and other subterranean facilities that may carry enemy soldiers, terrorists, weapons, munitions and explosives and other materiel of war or terrorism such as may carry enemy soldiers, terrorists, weapons, munitions and explosives and other materiel of war or terrorism. The method is characterized by the steps of:

(1) using one or more sensors for collecting of infrared (IR) and visual data for imaging to within an area which may have such subsurface targets;

(2) using the one or more sensors to produce multi-spectral, bore-sighted images to locate and map specific types of such subsurface targets;

wherein the data is collected with temperature pattern thermal resolution of less than 75 milliKelvins (mK) and matching visual imagery;

(3) processing and storing the images with both analogue and digital hardware and software;

wherein the images may be in the format of still images, a series of still images, or a video sequence of images; and (4) analyzing and correlating between IR thermography data, visual data and location data and other relevant information which can be taken into consideration in relation to IR thermography data and visual data; and thereby identifying target signatures depending such targets being sought.

Such method is further characterized by using types of data enhancements to assist in target detection which are selected from the group consisting of but not limited to global and localized contrast, global and localized brightness, image size changes, global and localized blog analysis, pixel by pixel contrast enhancements, colorization, background image noise suppression, and orthorectification.

Such method is still further characterized by location and mapping of such subsurface targets by using in, in conjunction with the imaging sensing, a global positioning system (GPS) to facilitate target mapping.

In view of the foregoing description of the present invention and various embodiments and methods it will be seen that the several objects of the invention are achieved and other advantages are attained.

The illustrations and description explains general principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting.

What is claimed is:

1. A system for seeking, by remote sensing, subterranean targets including clandestine tunnels and other subterranean facilities capable of carrying enemy soldiers, terrorists, weapons, munitions, explosives, and other materiel of war or terrorism, by use of visual and thermal imagery, the system comprising:
 a remote infrared (IR) sensor configured for collecting IR thermography data for imaging an area potentially having subsurface targets, the IR sensor comprising a sight bore and configured to provide data collected with temperature pattern thermal resolution of less than 75 milliKelvins, the IR sensor producing multi-spectral, bore-sighted images to locate and map subsurface targets comprising tunnels, storage areas, underground chemical tanks, utility pipelines and conduits, construction debris, roadway asphalt, bridge deck asphalt, or concrete pavement internal cracks and voids;
 a remote light detection and ranging (LIDAR) detector configured for collecting visual imagery data for imaging the area potentially having subsurface targets;
 analogue and digital hardware and software configured for processing and storing multi-spectral, bore-sighted images produced by the sensors and configured for analysis, correlation, and orthorectification between IR thermography data collected by the remote IR sensor, and visual imagery data collected by the remote LIDAR detector, to provide target identification.

2. The system according to claim 1, wherein the remote IR detector is configured to capture still images, a series of still images, or a video sequence of images, 3. A method of identifying and mapping, as subsurface targets, clandestine tunnels and other subterranean facilities that are capable of carrying enemy soldiers, terrorists, weapons, munitions and explosives, and other materiel of war or terrorism comprising:
 collecting infrared (IR) thermography data and light detection and ranging (LIDAR) visual imagery data for imaging within an area capable of having subsurface targets, the IR thermography data having temperature pattern thermal resolution of less than 75 milliKelvins (mK);
 producing multi-spectral, bore-sighted images in the format of still images, a series of still images, or a video sequence of images, from the data collected;
 correlating and orthorectifying the IR thermography data and the LIDAR visual imagery data to identify target signatures; and
 mapping the target signatures identified.

4. The method as set forth in claim 3, wherein the IR thermography data and the LIDAR visual imagery data are enhanced with respect to global and localized contrast, global and localized brightness, image size changes, global and localized blog analysis, pixel by pixel contrast enhancements, colorization, background image noise suppression, or orthorectification.

5. The method as set forth in claim 3, wherein the IR thermography data is captured in the format of still images, a series of still images, or a video sequence of images.

6. The method as set forth in claim 3, wherein the correlating and orthorectifying comprises correlating and orthorectifying the IR thermography data, the LIDAR visual imagery data, and location data.

7. The method as set forth in claim 6, wherein the location data comprises global positioning system (GPS) data.

* * * * *